(12) United States Patent
Wiggin et al.

(10) Patent No.: US 9,492,302 B2
(45) Date of Patent: Nov. 15, 2016

(54) APPARATUS AND CLUTCH FOR USING CONTROLLED STORAGE AND RELEASE OF MECHANICAL ENERGY TO AID LOCOMOTION

(75) Inventors: Michael B. Wiggin, Raleigh, NC (US); Gregory S. Sawicki, Durham, NC (US); Steven H. Collins, Pittsburgh, PA (US)

(73) Assignee: North Carolina State University, Raleigh, NC (US)

( * ) Notice: Subject to any disclaimer, the term of this patent is extended or adjusted under 35 U.S.C. 154(b) by 1074 days.

(21) Appl. No.: 13/586,528

(22) Filed: Aug. 15, 2012

(65) Prior Publication Data

US 2013/0046218 A1    Feb. 21, 2013

Related U.S. Application Data

(60) Provisional application No. 61/523,507, filed on Aug. 15, 2011.

(51) Int. Cl.
*A61H 3/00* (2006.01)
*A61F 5/00* (2006.01)
*A61F 5/01* (2006.01)

(52) U.S. Cl.
CPC ........... *A61F 5/0127* (2013.01); *A61F 5/0102* (2013.01); *A61H 3/00* (2013.01); *A61H 2201/12* (2013.01);
(Continued)

(58) Field of Classification Search
CPC .............. F16D 41/12; A61F 2202/6845; A61F 2202/685; A61F 2202/6836; A61F
(Continued)

(56) References Cited

U.S. PATENT DOCUMENTS 2,267,848 A  *  12/1941  Taylor .................. A61F 5/0102
                                                           602/16
2,439,100 A  *  4/1948  Richards ............... A61F 5/0127
                                                           602/28
(Continued)

FOREIGN PATENT DOCUMENTS

WO    WO 2011/129892 A9    10/2011

OTHER PUBLICATIONS

Bruno Jadim and Adriano A. G. Siqueira, "Development of Series Elastic Actuators for Impedance Control of an Active Ankle Foot Orthosis", 20th International Congress of Mechanical Engineering, Nov. 15-20, 2009.*

(Continued)

*Primary Examiner* — Justine Yu
*Assistant Examiner* — Tu Vo
(74) *Attorney, Agent, or Firm* — Jenkins, Wilson, Taylor & Hunt, P.A.

(57) ABSTRACT

The subject matter described herein includes an apparatus and a clutch for using controlled storage and release of mechanical energy to aid in locomotion. One exemplary apparatus includes a frame including an upper portion configured to mechanically couple to a leg of the subject on a calf side of an ankle joint of the subject and a lower portion pivotally attached to the upper portion configured to mechanically couple to a foot of the subject on a foot side of the ankle joint of the subject. The apparatus include a rotary clutch and an elastic element coupled between the upper and lower portions of the frame to control periods of energy storage and release by the elastic element.

19 Claims, 13 Drawing Sheets

(52) U.S. Cl.
CPC ............... *A61H 2201/1207* (2013.01); *A61H 2201/1253* (2013.01); *A61H 2201/16* (2013.01); *A61H 2201/1602* (2013.01); *A61H 2201/164* (2013.01); *A61H 2201/1642* (2013.01); *A61H 2205/10* (2013.01); *A61H 2205/106* (2013.01)

(58) Field of Classification Search
CPC ............... 5/0127;A43B 7/18; A43B 5/0452; A43B 5/0454; A43B 5/0456; A43B 5/046; A61H 1/0262; A61H 3/00; A61H 1/00; A61H 1/02; A61H 2001/0203; A61H 2201/0211; A61H 1/0237; A61H 2201/12; A61H 2201/14; A61H 2201/1445; A61H 2201/1481; A61H 2201/149; A61H 2201/164; A61H 2201/1642; A61H 2205/12; A61H 2205/106
USPC ............ 192/46; 623/40–52; 601/5; 269/143, 269/249; 36/88, 89, 118.3, 118.4, 118.5; 602/16, 20–28
See application file for complete search history.

(56) References Cited

U.S. PATENT DOCUMENTS

| | | | | |
|---|---|---|---|---|
| 2,525,237 A * | 10/1950 | Park | ............ | A61F 5/0127 602/28 |
| 2,536,454 A * | 1/1951 | McIntyre | ............ | A61F 5/0102 602/28 |
| 2,573,347 A * | 10/1951 | Mazzola | ............ | A61F 2/604 242/147 R |
| 2,652,570 A * | 9/1953 | Sargeson | ............ | A61F 2/588 623/63 |
| 2,710,974 A * | 6/1955 | Motis | ............ | A61F 2/58 623/63 |
| 4,067,070 A * | 1/1978 | Seamone | ............ | A61F 2/58 623/24 |
| 4,688,559 A * | 8/1987 | Vito | ............ | A61F 5/0102 602/23 |
| 5,112,296 A * | 5/1992 | Beard | ............ | A61F 5/0113 128/905 |
| 6,171,272 B1 * | 1/2001 | Akita | ............ | A61F 5/0127 602/27 |
| 6,666,796 B1 * | 12/2003 | MacCready, Jr. | ............ | A61F 5/0102 135/65 |
| 8,075,633 B2 | 12/2011 | Herr et al. | | |
| 2004/0064195 A1 * | 4/2004 | Herr | ............ | A61F 2/66 623/24 |
| 2005/0070834 A1 * | 3/2005 | Herr | ............ | A61B 5/1038 602/28 |
| 2005/0251079 A1 * | 11/2005 | Carvey | ............ | A61F 5/0102 602/26 |
| 2007/0043449 A1 * | 2/2007 | Herr | ............ | A61F 2/60 623/24 |
| 2007/0267791 A1 * | 11/2007 | Hollander | ............ | F16F 1/125 267/177 |
| 2010/0076346 A1 | 3/2010 | Abel et al. | | |
| 2010/0185301 A1 * | 7/2010 | Hansen | ............ | A61F 2/6607 623/47 |
| 2013/0289452 A1 * | 10/2013 | Smith | ............ | B25J 9/0006 601/33 |

OTHER PUBLICATIONS

Arumugom. S, Muthuraman.S, Ponselvan.V, "Modeling and Application of Series Elastic Actuators for Force Control Multi Legged Robots", Journal of Computing, vol. I, Issue 1, Dec. 2001.*

Wiggin, "A Passive-Elastic Ankle Exoskeleton Using Controlled Energy Storage and Release," pp. 1-2 (May 2011).

Collins et al., "Recycling Energy to Restore Impaired Ankle Function during Human Walking," PLoS One, vol. 5, Issue 2, e9307, pp. 1-6 (Feb. 2010).

Sawicki et al., "It Pays to Have a Spring in Your Step," Exercise and Sport Sciences Reviews, vol. 37, pp. 130-138 (Jul. 2009).

Herr, "Exoskeletons and orthoses: classification, design challenges and future directions," Journal of NeuroEngineering and Rehabilitation, vol. 6, 21 pgs. (Jun. 18, 2009).

Sawicki et al., "Powered ankle exoskeletons reveal the metabolic cost of plantar flexor mechanical work during walking with longer steps at constant step frequency," Journal of Experimental Biology, vol. 212, pp. 21-31 (Jan. 2009).

Sawicki et al., "Mechanics and energetics of incline walking with robotic ankle exoskeletons," Journal of Experimental Biology, vol. 212, pp. 32-41 (Jan. 2009).

Sawicki et al., "Mechanics and energetics of level walking with powered ankle exoskeletons," Journal of Experimental Biology, vol. 211, pp. 1402-1413 (May 2008).

Dollar et al., "Lower Extremity Exoskeletons and Active Orthoses: Challenges and State-of-the-Art," IEEE Transactions on Robotics, vol. 24, No. 1, pp. 144-158 (Feb. 2008).

Walsh et al., "A quasi-passive leg exoskeleton for load-carrying augmentation," International Journal of Humanoid Robotics, vol. 4, No. 3, pp. 487-506 (Sep. 2007).

Ferris et al., "A Physiologist's Perspective on Robotic Exoskeletons for Human Locomotion," International Journal of Humanoid Robotics, vol. 4, No. 3, pp. 507-528 (Sep. 2007).

Doke et al., "Energetic cost of producing cyclic muscle force, rather than work, to swing the human leg," Journal of Experimental Biology, vol. 210, pgs. 2390-2398 (Jul. 2007).

Zoss et al., "Design of an electrically actuated lower extremity exoskeleton," Advanced Robotics, vol. 20, pp. 967-988 (2006).

Ishikawa et al., "Muscle-tendon interaction and elastic energy usage in human walking," J Appl Physiol, vol. 99, pp. 603-608 (Aug. 2005).

Sawicki et al., "Powered Lower Limb Orthoses: Applications in Motor Adaptation and Rehabilitation," IEEE International Conference on Rehabilitation Robotics, pp. 206-211 (Jun.-Jul. 2005).

Doke et al., "Mechanics and energetics of swinging the human leg," Journal of Experimental Biology, vol. 208, pp. 439-445 and Erratum (Feb. 2005).

Jacobsen et al., "Research Robots for Applications in Artificial Intelligence, Teleoperation and Entertainment," International Journal of Robotics Research, vol. 23, pp. 319-330 (Apr.-May 2004).

* cited by examiner

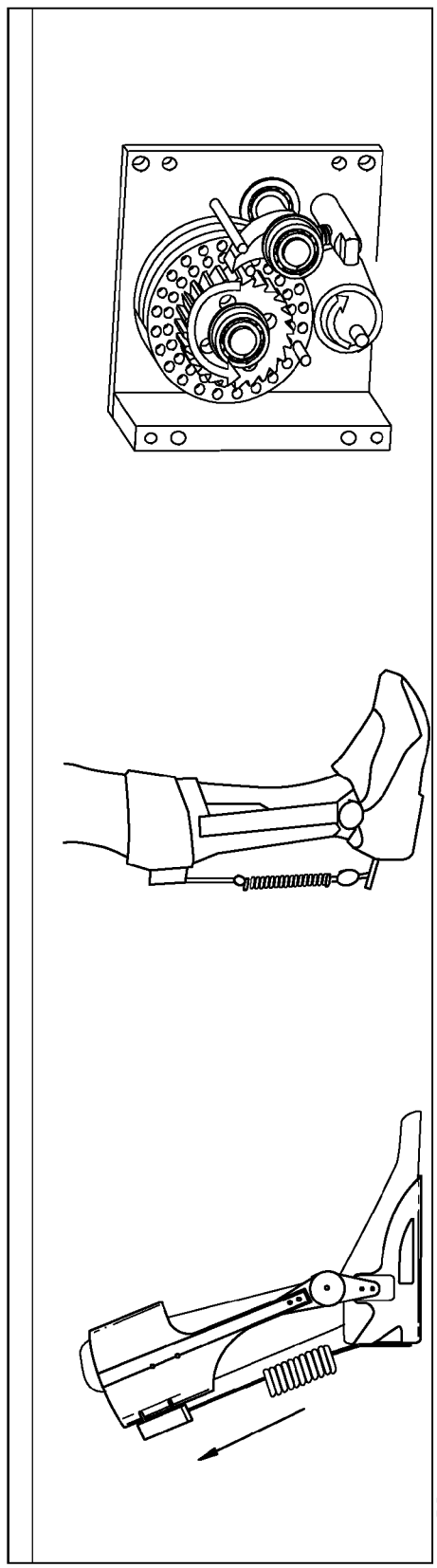
FOOT FLAT
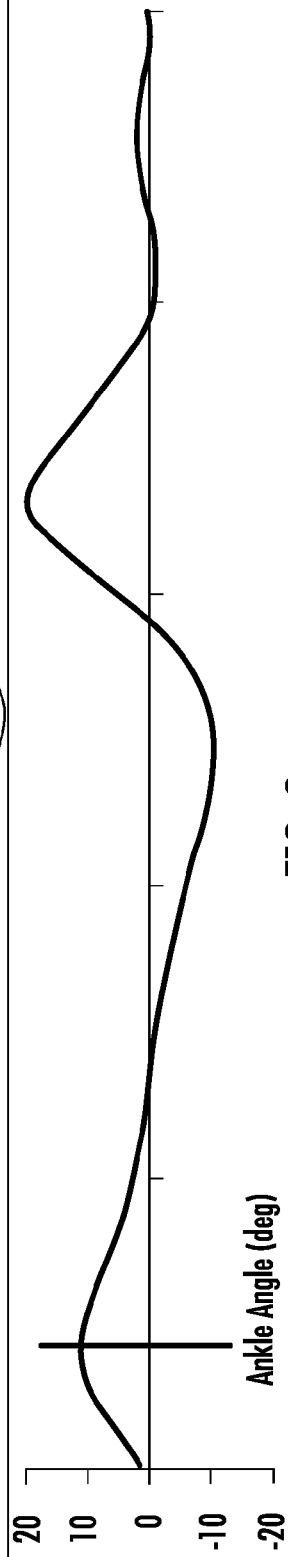
FIG. 8
Ankle Angle (deg)

DORSIFLEXION

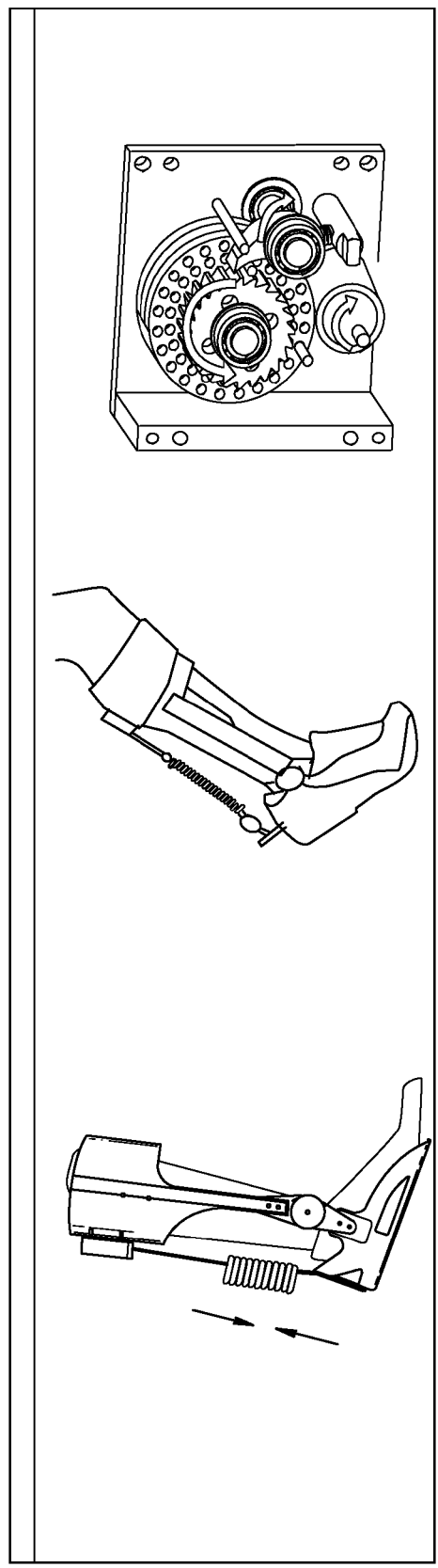
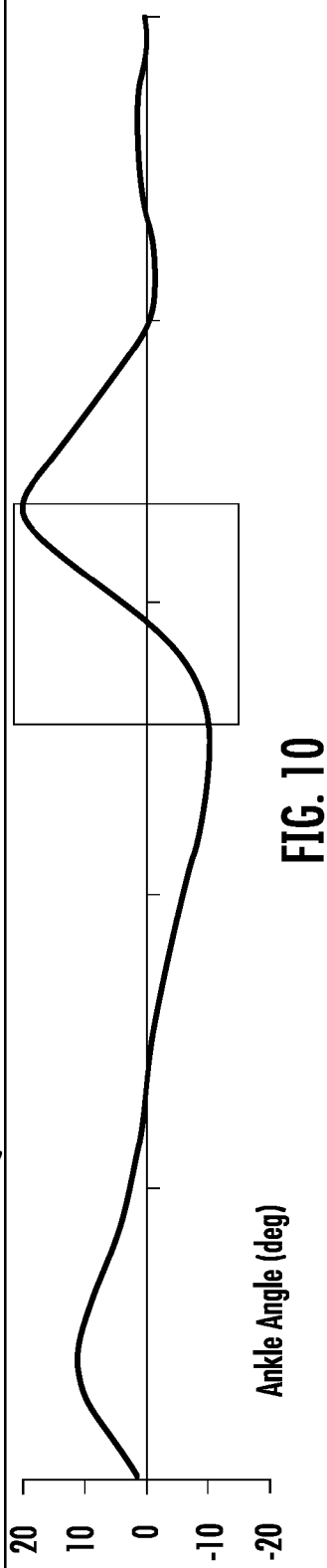
DORSIFLEXION
FIG. 10
Ankle Angle (deg)

APPARATUS AND CLUTCH FOR USING CONTROLLED STORAGE AND RELEASE OF MECHANICAL ENERGY TO AID LOCOMOTION

PRIORITY CLAIM

This application claims the benefit of U.S. Provisional Patent Application Ser. No. 61/523,507, filed Aug. 15, 2011; the disclosure of which is incorporated herein by reference in its entirety.

TECHNICAL FIELD

The subject matter described herein relates to mechanical energy storage and release. More particularly, the subject matter described herein relates to an apparatus and a clutch for using controlled storage and release of mechanical energy to aid locomotion.

BACKGROUND

Ankle foot orthoses (AFO) are devices that are worn by individuals to aid in walking. For example, humans with disabilities caused by stroke, cerebral palsy, spinal cord or brain injury, or other musculoskeletal disorders or injuries may have limited strength in the muscles that control the ankle joint. AFO devices are worn by such individuals to either aid in locomotion or prevent further injury.

One problem with some existing AFO devices is that they contain active components, such as motors, to assist in locomotion. Using active components requires an onboard power supply which increases the weight and the complexity of such devices. Other AFO devices are purely mechanical but are not designed to assist in locomotion. For example, some devices attempt to restrict angular movement of the ankle joint to prevent toe drop, foot drag, or other abnormal conditions during walking caused by impairment.

Accordingly, in light of these difficulties, there exists a need for an improved apparatus and a clutch for using controlled storage and release of mechanical energy to aid locomotion.

SUMMARY

The subject matter described herein includes an apparatus and a clutch for using controlled storage and release of mechanical energy to aid in locomotion. One exemplary apparatus comprises a frame including an upper portion configured to mechanically couple to a leg/shank of the subject above the ankle joint of the subject on the calf side and a lower portion pivotally attached to the upper portion configured to mechanically couple to a foot of the subject below the ankle joint of the subject on the foot side. The apparatus includes a rotary clutch and an elastic element coupled between the upper and lower portions of the frame to control periods of energy storage and release by the elastic element.

The subject matter described herein further includes a clutch for controlling storage and release of mechanical energy by an elastic element to aid in locomotion of a subject. The clutch includes a housing configured to couple to the frame of an ankle foot orthotic device. The clutch further includes a rotatable drum (i.e. pulley) coupled to the housing for extending and retracting a linkage configured to couple to an elastic element of the ankle foot orthotic device. The clutch further includes a ratchet coupled to the drum. The clutch further includes a pawl coupled to the housing for engaging and disengaging with the ratchet to allow and prevent rotation of the drum. The clutch further includes at least one structure coupled to the housing to control the engaging and disengaging of the pawl with the ratchet and thereby control periods of energy storage and release of the elastic element.

BRIEF DESCRIPTION OF THE DRAWINGS

Preferred embodiments of the subject matter described herein will now be explained with reference to the accompanying drawings, of which:

FIG. 8 is a diagram illustrating operation of the clutch during the foot flat stage of walking according to an embodiment of the subject matter described herein;

FIG. 10 is a diagram illustrating operation of the clutch during the push off phase of walking according to an embodiment of the subject matter described herein;

DETAILED DESCRIPTION

Figure 1:
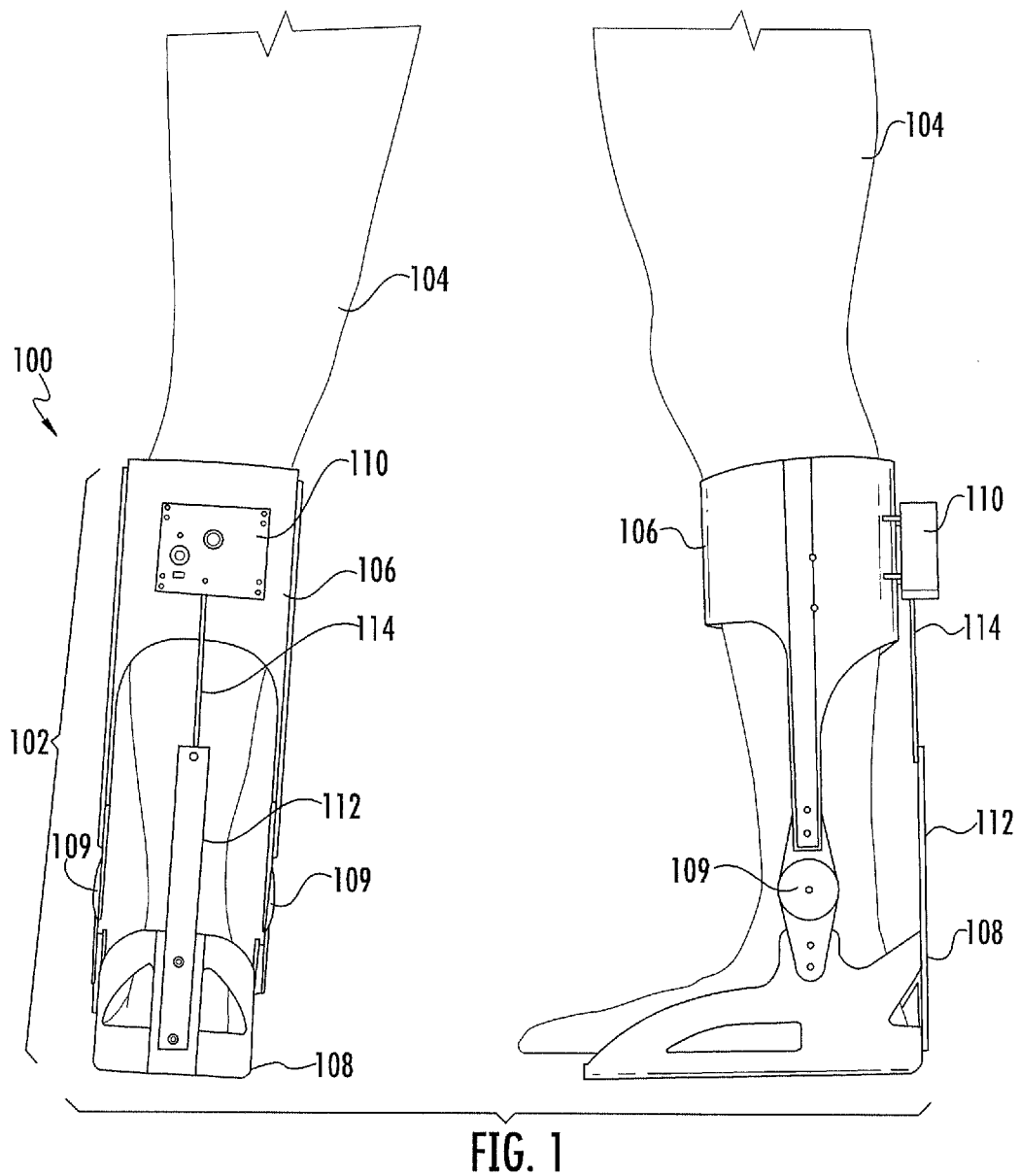
FIG. 1 is a rear view and a side view of an apparatus for controlled storage and release of mechanical energy to assist in locomotion according to an embodiment of the subject matter described herein.

The subject matter described herein includes an apparatus and a clutch for controlled storage and release of mechanical energy. FIG. 1 is a rear view and a side view of an apparatus for controlled storage and release of mechanical energy to assist in locomotion according to an embodiment of the subject matter described herein. Referring to FIG. 1, an apparatus 100 comprises an AFO device including a frame 102 that forms an exoskeleton configured to fit around the lower leg of a user 104. Frame 102 includes an upper portion 106 configured to enclose a portion of the user's leg on the calf side of the user's ankle joint and a lower portion 108 configured to surround a portion of the user's foot on a foot side of the user's ankle joint. Frame 102 provides support at three points: under the ball of the foot, at the heel of the foot, and about the shank of the leg below the knee. Frame 102 may be primarily composed of a lightweight compound, such as a carbon fiber material or aluminum, and provides a mechanical support structure for the exoskeleton. Frame 102 transmits forces from the exoskeleton to the user's lower limb. Upper portion 106 is coupled to lower portion 108 via hinges 109. In an alternate embodiment that will be described below, lower portion 108 comprises a shoe.

A clutch 110 and an elastic element 112 are coupled between upper portion 106 and lower portion 108 to control storage and release of mechanical energy by elastic element 112. In the illustrated example, clutch 110 is attached to upper portion 106 and elastic element 112 is attached to lower portion 108. However, clutch 110 can be attached to lower portion 108, and elastic element 112 can be attached to upper portion 106 without departing from the scope of the subject matter described herein. Clutch 110 may be rigidly attached to frame 102 at the back of upper portion 106. As will be described in detail below, clutch 110 may include a system of springs, gears, and mechanical constraints to set periods of energy storage and return based off of the user's ankle configuration. The user's ankle configuration is coupled to clutch 110 due to the mechanical linkage between clutch 110 and frame 102.

Elastic element 112 is attached between clutch 110 and the posterior distal (heel) section of lower portion 108 of frame 102. This allows elastic energy captured to be directly transmitted about the ankle joint, thus assisting plantar flexion and forward propulsion. In the illustrated example, elastic element 112 comprises an elongate elastomeric member that stretches in the direction of applied force. For example, elastic element 112 may be formed of rubber or other elastomeric material that stretches in the direction of applied force.

Clutch 110 is attached to elastic element 112 via a linkage 114. Linkage 114 is preferably formed of a material that is more rigid than elastic element 112 in a direction of force application to linkage 114 along its axis when linkage 114 is taught. As will be described in detail below, clutch 110 comprises a rotary clutch configured to selectively engage, lock, and disengage during different phases of walking to store energy in elastic element 112 and release energy stored in elastic element 112 to aid in locomotion.

Figure 2:
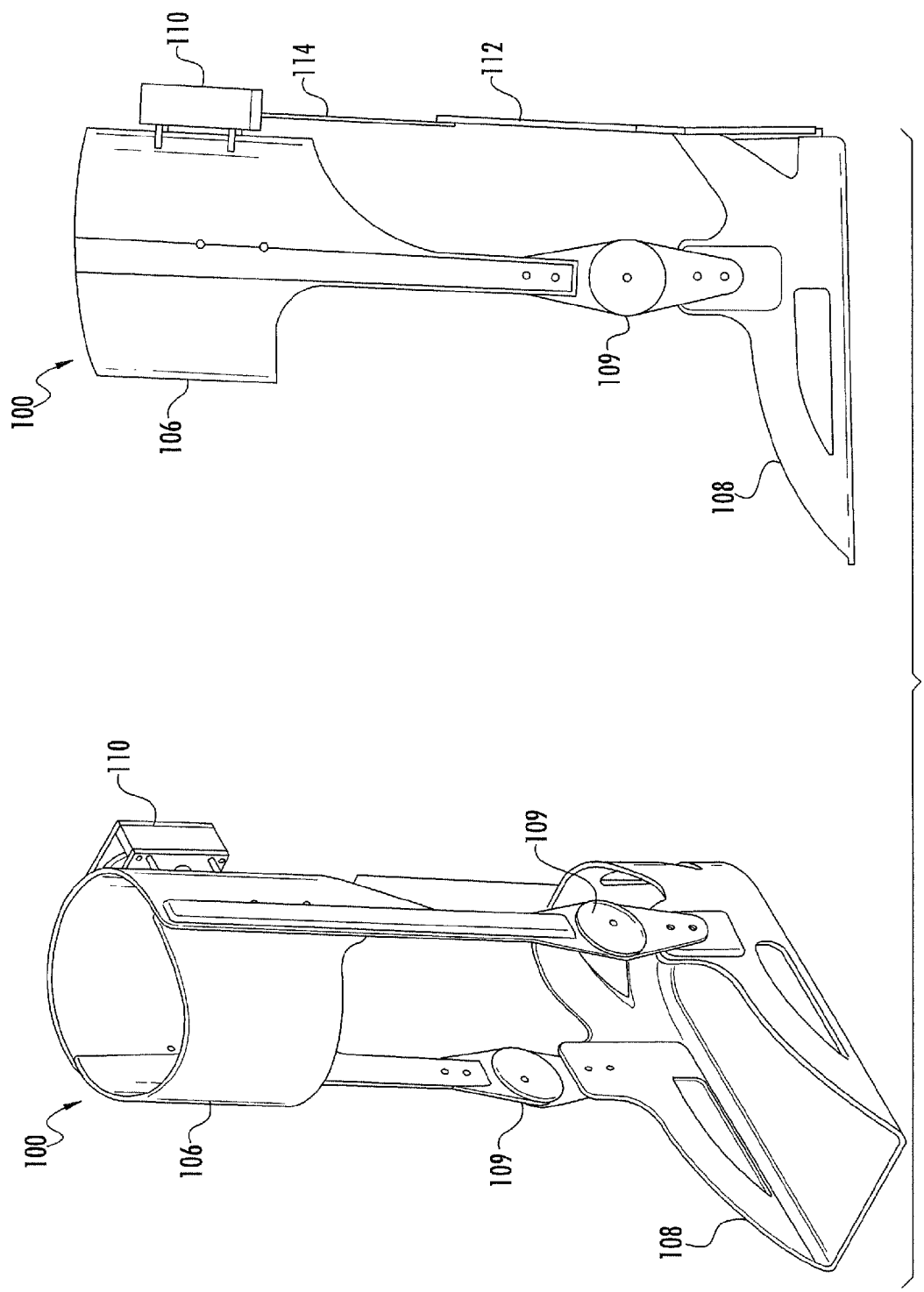
FIG. 2 is a front perspective view and a side view of an apparatus for controlled storage and release of mechanical energy to assist in locomotion according to an embodiment of the subject matter described herein.

FIG. 2 is a front perspective view and a side view of apparatus 100. In the illustrated embodiment, it can be seen that lower portion 108 is configured to fit under an individual's foot and that upper portion 106 is annular and configured to surround an individual's calf. Clutch 110 is fixedly attached to upper portion 106 via screws, bolts, or other suitable attachment mechanism. From the side view, it can be seen that as hinges 109 pivot during dorsiflexion, the angle between upper portion 106 and lower portion 108 becomes smaller, elastic element 112 stretches from its resting position and stores energy. Linkage 114 extends from and retracts into clutch 114. As will be described in more detail below, when clutch 110 locks, extraction of linkage 114 from clutch 110 is prevented, and energy is stored in elastic element 112.

Figure 3:
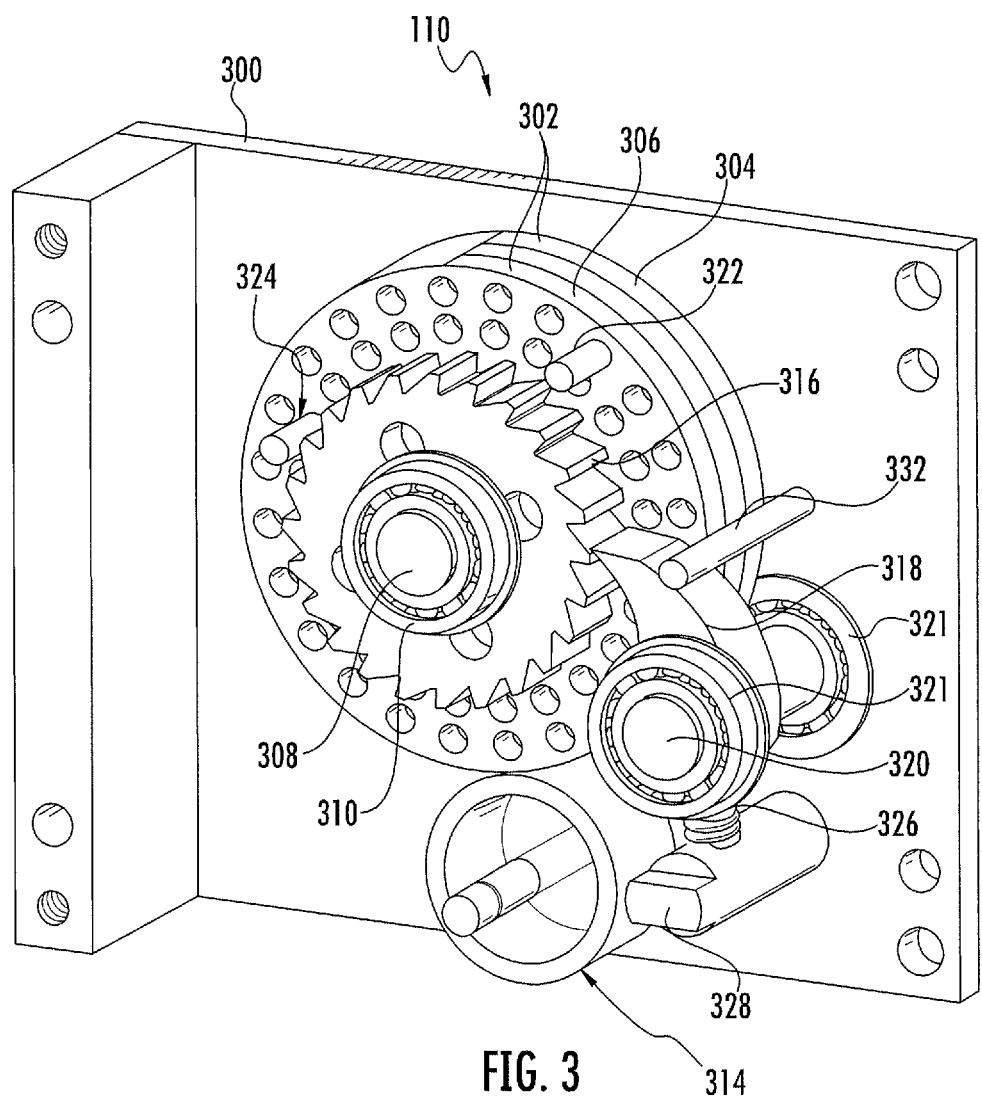
FIG. 3 is a front perspective view of a clutch suitable for use in an apparatus for controlled storage and release of mechanical energy according to an embodiment of the subject matter described herein.
Figure 4:
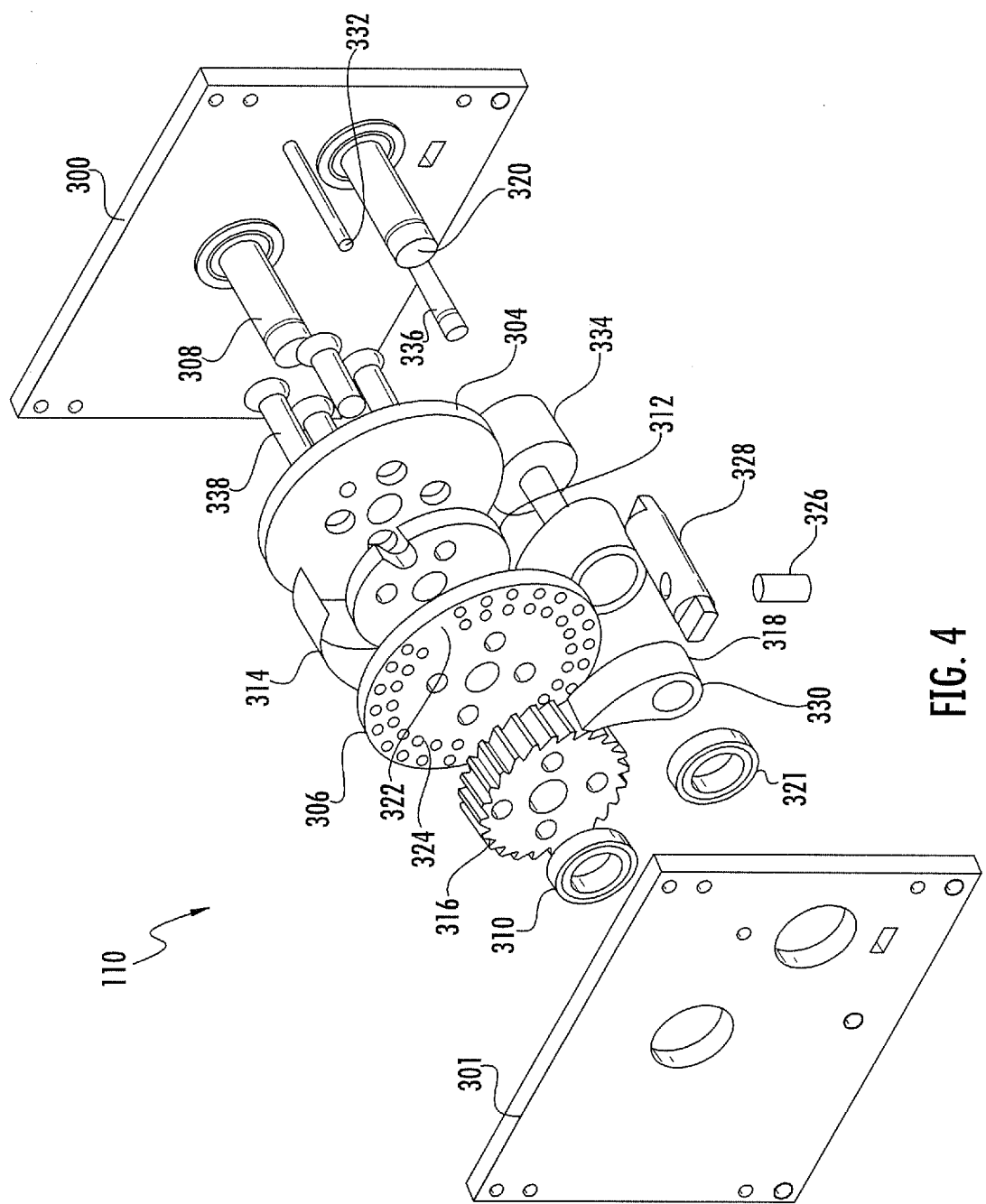
FIG. 4 is an exploded view of the clutch illustrated in FIG. 3.

FIG. 3 is a perspective view and FIG. 4 is an exploded view of clutch 110. Clutch 110 includes a housing formed by an inner portion 300 and outer portion 301. In FIG. 3, outer portion 301 is omitted. Clutch 110 includes a rotating drum 302 formed by a back retainer 304 and a timing pin holder 306. Drum 302 rotates about a rod 308 via roller bearing assembly 310. A pulley 312 is located between back retainer 304 and timing pin holder 306. Pulley 312 is attached to linkage 114 (illustrated in FIGS. 1 and 2) to allow extraction of linkage 114 from clutch 110 and retraction of linkage 114 into clutch 110. A return spring 314 applies a counterclockwise torque to drum 302 to effect retraction of linkage 114 when the force applied to linkage 114 is less than that applied by spring 314.

Figure 5:
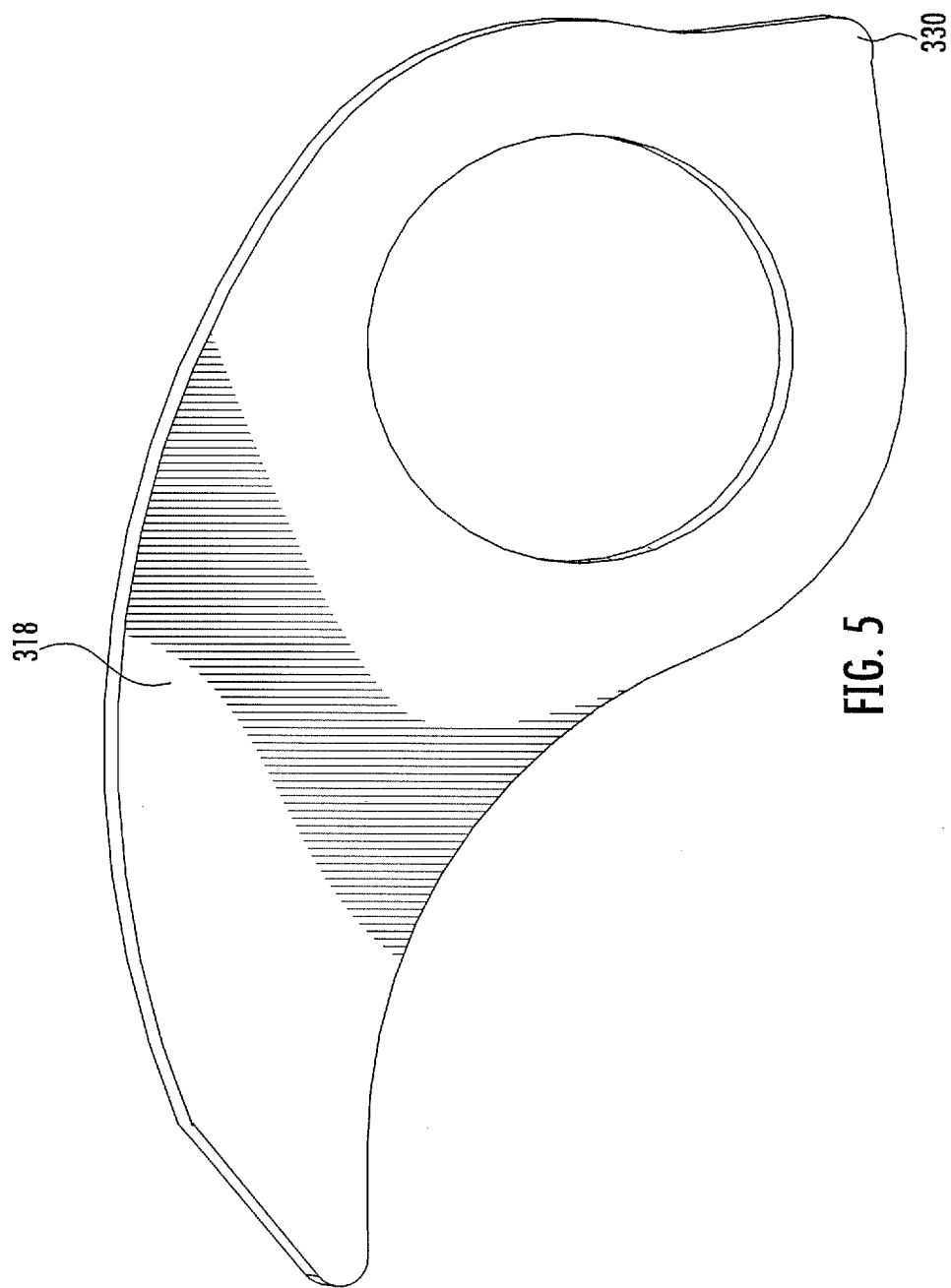
FIG. 5 is a perspective view of a pawl suitable for use in the clutch illustrated in FIG. 3.

In order to provide an engagement and locking mechanism to control energy storage and release by elastic element 112 (illustrated in FIGS. 1 and 2), clutch 110 includes a rotary ratchet 316 and a pawl 318. Ratchet 316 is coupled to timing pin holder 306 and rotates with timing pin holder 306. Pawl 318 is mounted on a shaft 320 that rotates with respect to inner and outer portions 300 and 301 of the housing. Roller bearing assemblies 321 allow pawl 318 to rotate on shaft 320. A pair of timing pins 322 and 324 control the engagement and disengagement of pawl 318 with ratchet 316. A detent pin 326 mounted in a detent pin holder 328 contact one of two sides of a structure 330 formed on the end of pawl 318 that does not engage ratchet 316. Structure 330 is most clearly illustrated in FIG. 5. As illustrated in FIG. 5, structure 330 comprises a protrusion with sides that face in different directions. When detent pin 326 engages either of the sides, pawl 318 will be held in the corresponding angular position, which is either away from or engaging with ratchet 316. A stopping pin 332 limits angular rotation of pawl 318 in a direction away from ratchet 316.

As stated above, spring 314 retracts linkage 114 into clutch 110. To effect this retraction, as illustrated most clearly in FIG. 4, a portion of spring 314 is fixedly attached to and at least partially circumferentially surrounds pulley 312. Another portion of spring 312 is fixedly attached to and surrounds a spring holder 334, which rotationally attaches spring 314 to a spring shaft 336. When pulley 312 rotates in the clockwise direction, spring 314 is wound from its resting position, and spring holder 334 rotates in a counterclockwise direction about shaft 336. This winding motion causes spring 314 to store mechanical energy. When the force on linkage 114 becomes less than the reaction applied by spring 314, spring 314 unwinds, causing the portion of the spring that surrounds shaft 336 to rotate in the clockwise direction and effecting rotation of pulley 312 in the counterclockwise direction to retract linkage 114. Additional structures illustrated in FIG. 4 that are not described with respect to FIG. 3 are fasteners 338 which may be screws, bolts, or other suitable fastening structures, which hold back retainer 304, pulley 312, timing pin holder 306, and ratchet 316 together.

Figure 6:
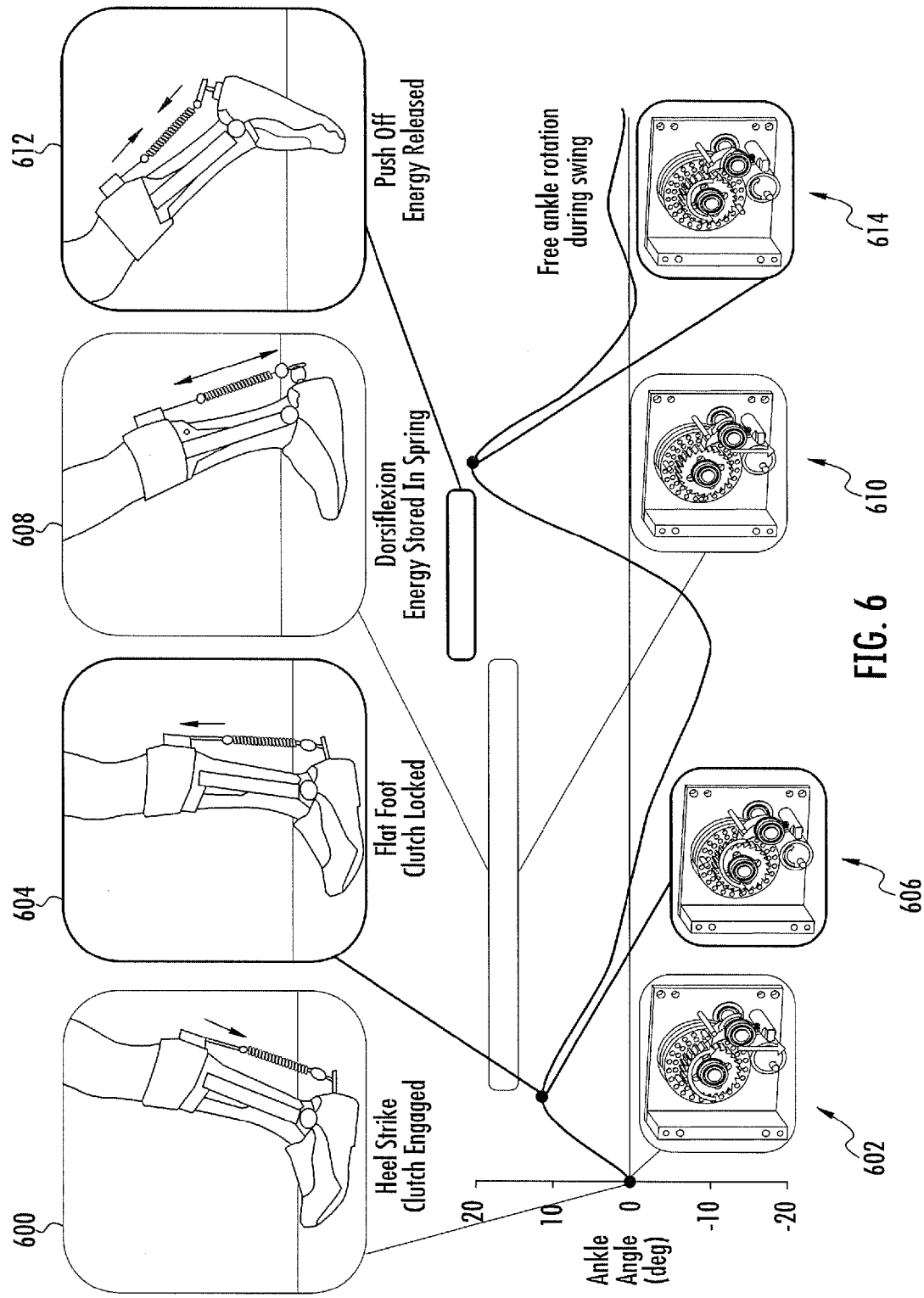
FIG. 6 is a diagram illustrating operation of the clutch for controlled storage and release of mechanical energy according to an embodiment of the subject matter described herein.
Figure 7:
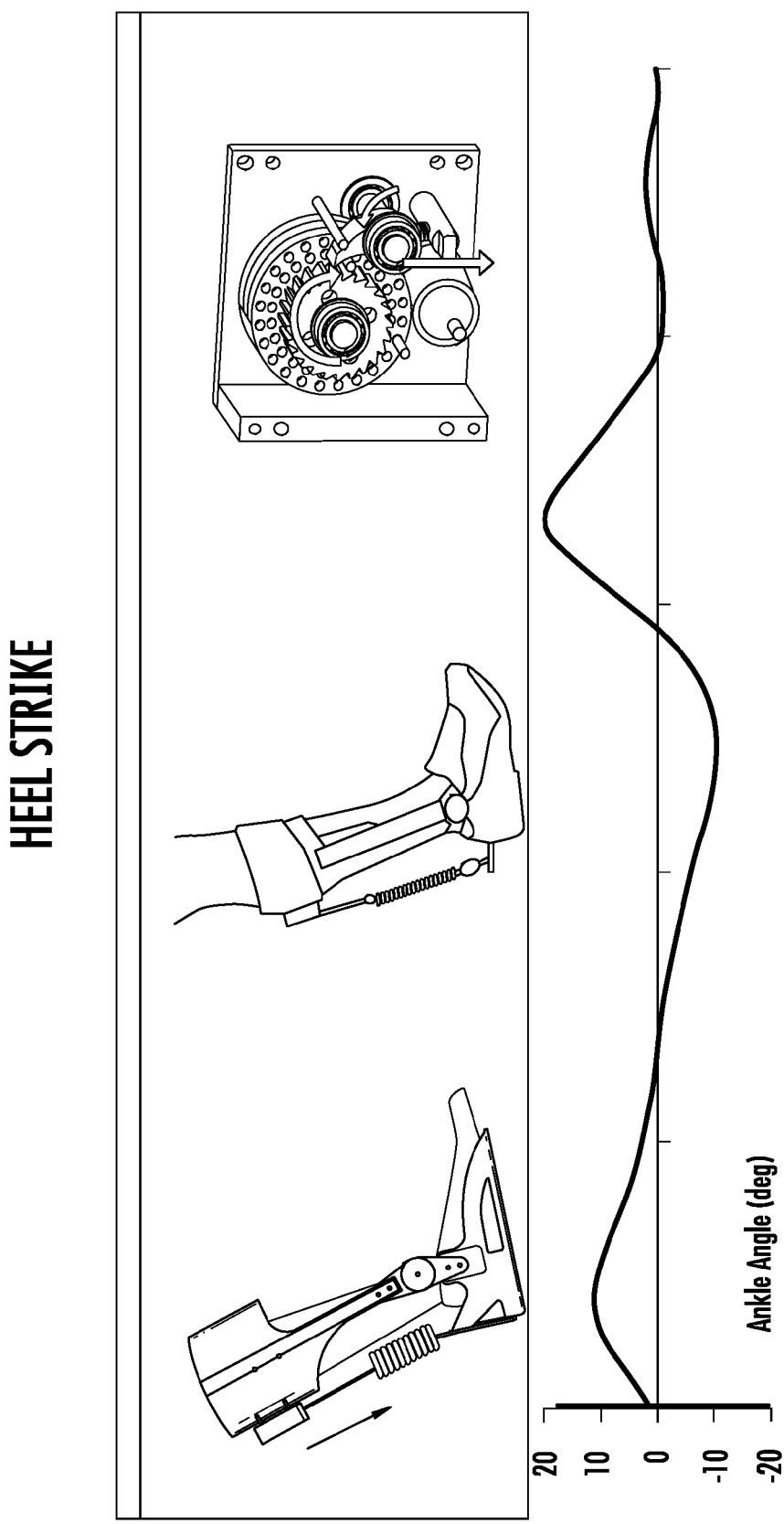
FIG. 7 is a diagram illustrating operation of the clutch during the heel strike stage of walking according to an embodiment of the subject matter described herein.
Figure 9:
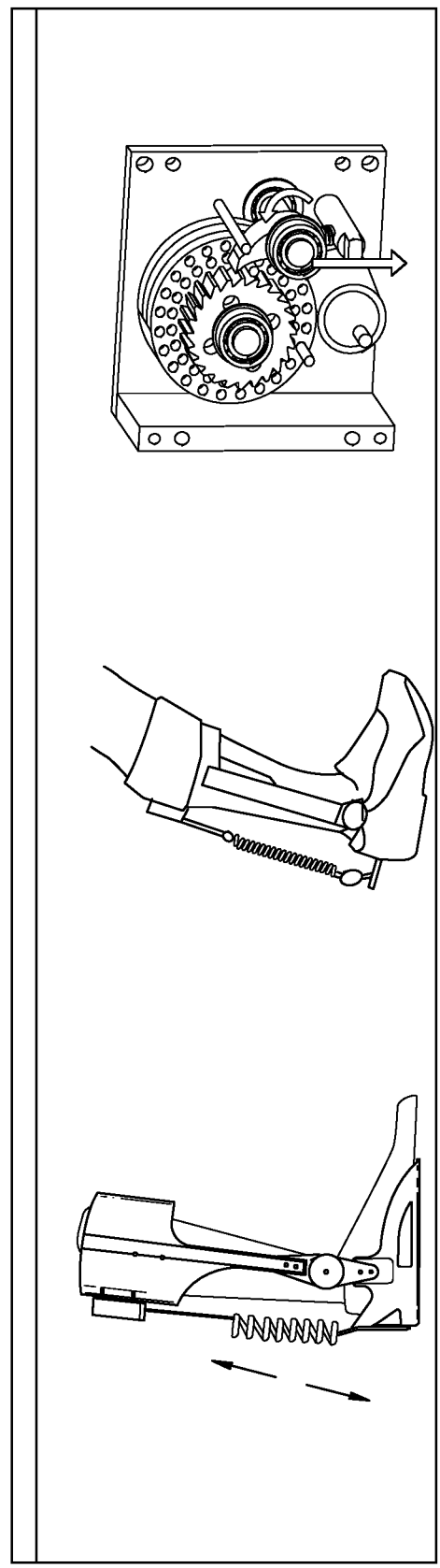
FIG. 9 is a diagram illustrating operation of the clutch during the dorsiflexion phase of walking according to an embodiment of the subject matter described herein.

FIG. 6 illustrates the various phases of walking and the corresponding positions of clutch 110. As illustrated by image 600 and the corresponding clutch position 602, just prior to heel strike, clockwise movement of pin holder 306 under force applied by linkage 114 causes timing pin 322 to engage pawl 318 with ratchet 316. Once engaged, motion of ratchet 316 is only allowed in the counterclockwise direction, which occurs from heel strike to foot flat position under force of spring 314 to retract linkage 114 into clutch 110. In the foot flat position, as illustrated by image 604 and the corresponding clutch position 606, the clutch is locked because linkage 114 and elastic element 112 apply clockwise force/torque on ratchet 316, and motion in the clockwise direction is prevented by the shapes of the teeth in ratchet 316 and the corresponding shape of pawl 318.

As illustrated by image 608 and corresponding clutch position 610, during dorsiflexion, when the clutch is locked, elastic element 112 stretches from its resting position and stores mechanical energy produced by the user's center of mass rotating over the ankle (during stance dorsiflexion). As illustrated by image 612 and corresponding clutch position 614, during push off (stance plantar flexion), the energy stored in elastic element 112 is released, aiding in locomotion of the subject. Timing pin 324 contacts pawl 318 and causes pawl 318 to release from ratchet 316 to allow free rotation of the ankle joint during the foot swing phase of walking prior to the next heel strike. FIGS. 7, 8, 9, and 10 are close-up views of clutch position during heel strike, foot flat, dorsiflexion, and push off, respectively.

According to an aspect of the subject matter described herein, clutch 110 is adjustable to change the periods of energy storage and release to match the gait of the subject. For example, the positions of timing pins 322 and 324 can be changed in timing pin holder 306 to change the periods of energy storage and release. Moving pins 322 and 324 to different holes in timing pin holder 306 changes the periods of energy storage and release by changing the times when pawl 318 engages with and disengages from ratchet 316.

Figure 11:
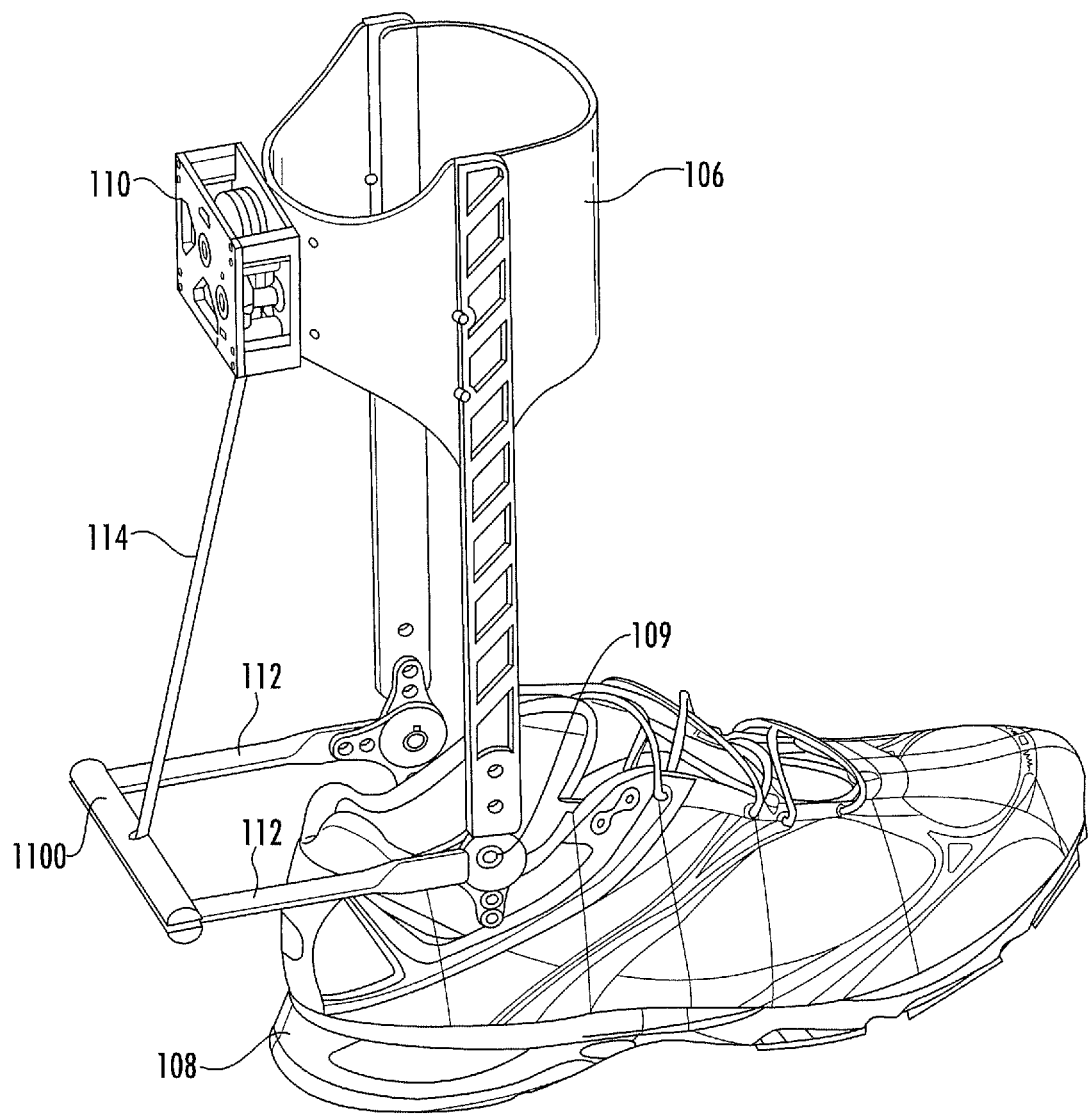
FIG. 11 is a diagram of an apparatus for controlled storage and release of mechanical energy according to an alternate embodiment of the subject matter described herein.

It should be noted that in FIG. 6, elastic element 112 comprises a coil spring, rather than an elongate elastomeric member, as illustrated in FIGS. 1 and 2. Any type of element capable of efficiently storing mechanical energy in response to an applied stress and releasing the mechanical energy when the stress is removed is intended to be within the scope of the subject matter described herein. In yet another alternate embodiment of the subject matter described herein, elastic element 112 may comprise a pair of composite elements bend in a direction transverse to the direction of force application by linkage 114. FIG. 11 illustrates such an embodiment. Referring to FIG. 11, elastic elements 112 are located on opposite sides of lower portion 108 of the frame, where lower portion 108 comprises a shoe or a mechanism for attaching to a shoe. A cross member 1100 couples elastic elements 112 to linkage 114. Elastic elements 112 store mechanical energy by bending in the direction of linkage 114 in response to applied force and release the energy when the applied stress is removed, as with the previously described embodiments. Elastic elements 112 may be made of any suitable material that is capable of efficient energy storage and release. In one example, elastic elements 112 may be made of a composite carbon material, similar to that used in forming a hunting or target bow.

Figure 12A:
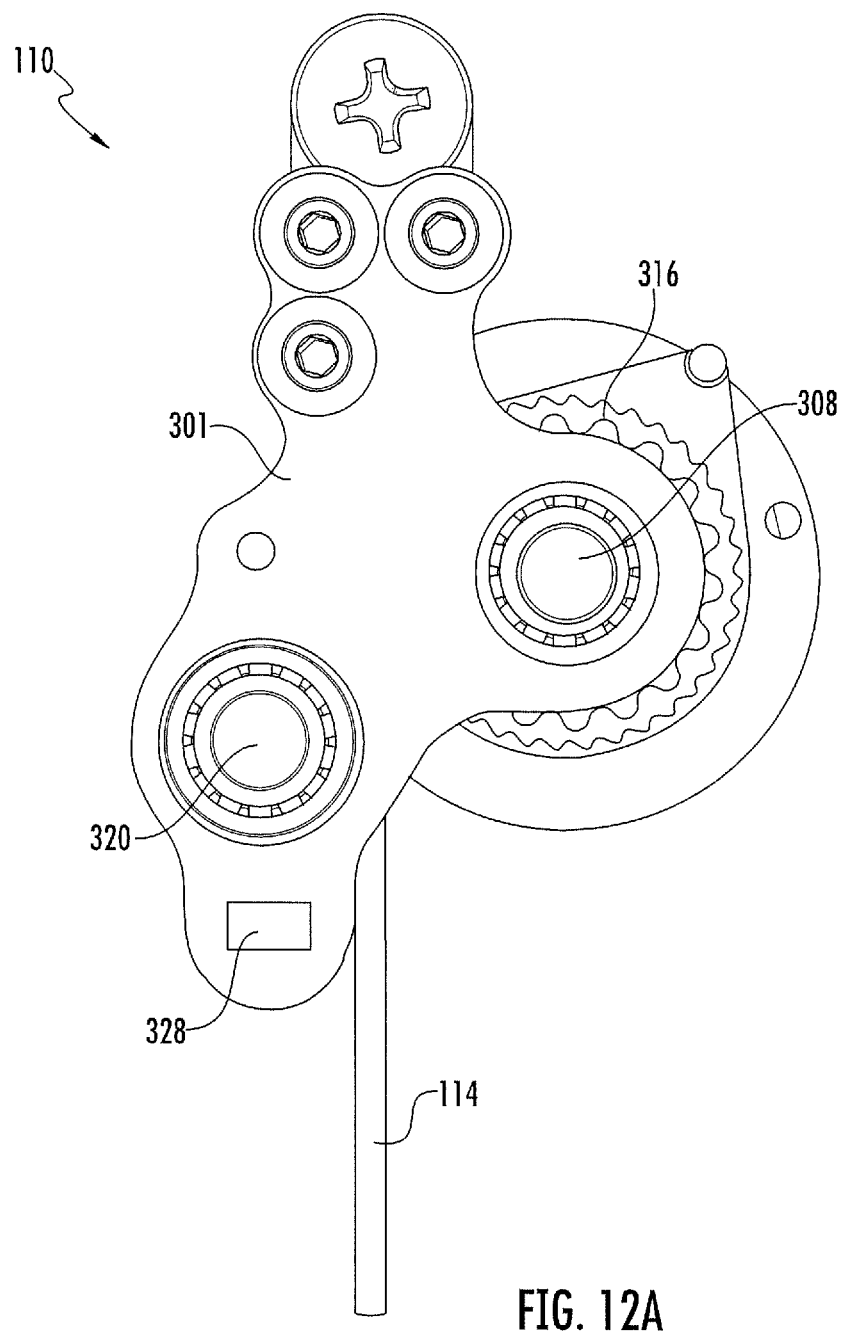
FIGS. 12A and 12B are diagrams illustrating an alternate design for a clutch according to an embodiment of the subject matter described herein.
Figure 12B:
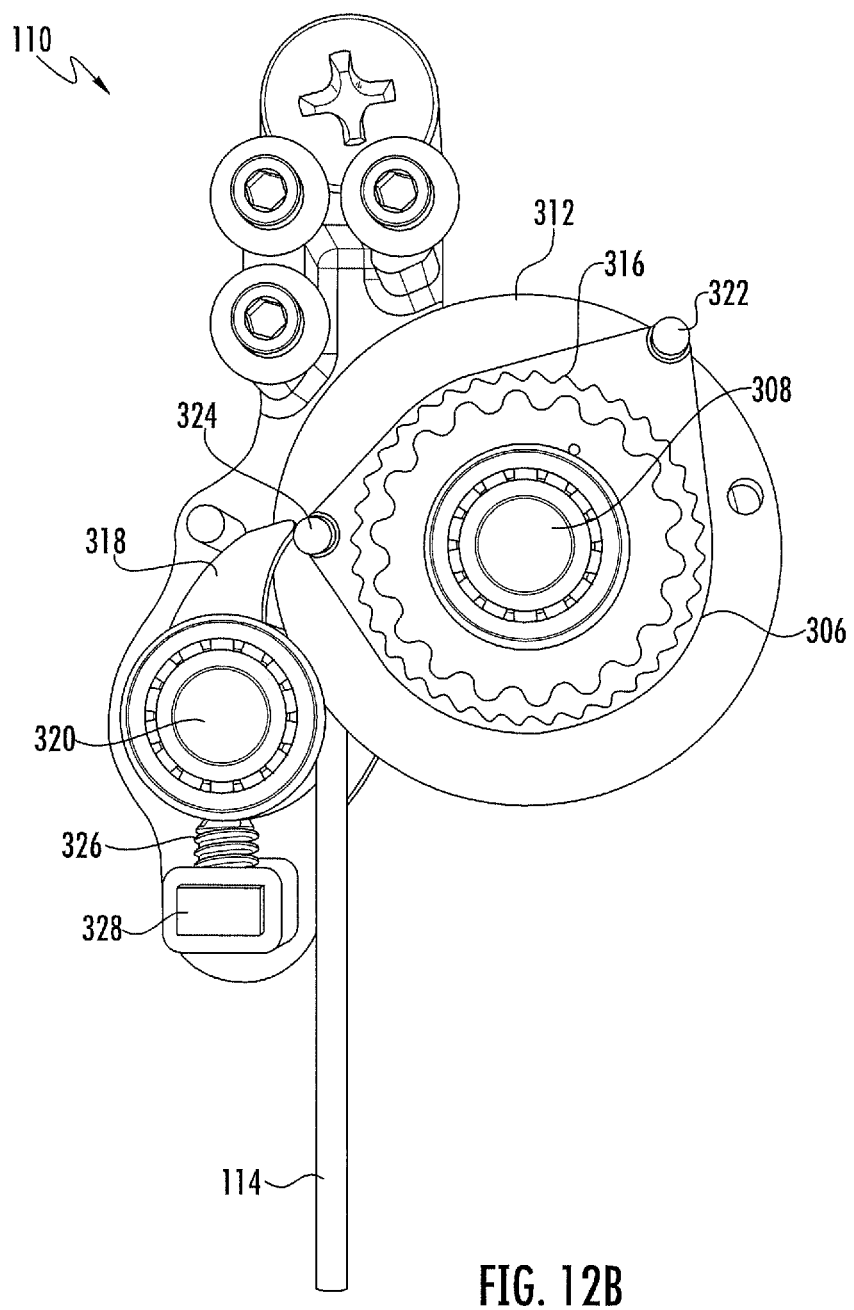

FIGS. 12A and 12B illustrate an alternate embodiment of clutch 110 according to an embodiment of the subject matter described herein. In FIG. 12A, outer portion 301 of the clutch housing is shown, and in FIG. 12B, outer portion 301 is omitted. The operation of clutch 110 in FIGS. 12A and 12B is the same as that described above with respect to the clutch illustrated in FIGS. 3 and 4. However, clutch 110 illustrated in FIGS. 12A and 12B is more compact in design and requires less material than the clutch illustrated in FIGS. 3 and 4. For example, it can be seen from the design of outer portion 301 in FIG. 12A that outer portion 301 only partially covers the internal components of clutch 110, which results in a smaller and more lightweight housing than in the embodiment illustrated in FIGS. 3 and 4. In addition, ratchet 316 and timing pin holder 306 are of different configurations that the corresponding parts illustrated in FIGS. 3 and 4.

In the examples described above, apparatus 100 is completely passive, requiring no on-board or external electric power. In an alternate embodiment, apparatus 100 may include a low-power electromechanical component, such as a servomotor within clutch 110 to control the engagement and disengagement of pawl 318 with ratchet 316. In addition, in the examples described above, clutch 110 is engaged, locked, and disengaged by purely mechanical feedback signals controlled by timing pins 322 and 324 and the direction of applied force. In an alternate embodiment, clutch 110 may be engaged, locked, and disengaged by an electrical signal, such as an electrical signal produced in response to a biological stimulus. In one example, the biological stimulus may be an electromyography signal produced from an electrode attached to the surface of the subject's skin near a muscle of interest, such as the subject's calf muscle. Clutch 110 may also be adjustable to account for changes in locomotion conditions other than gait, such as ground slope.

Apparatus 100 functions because the body has a significant amount of center of mass energy that is normally stored, dissipated, or returned by the Achilles tendon. Apparatus 100 is essentially an external artificial Achilles tendon and calf muscle. Elastic element 112 is modeled after the Achilles tendon and aponeurosis, and clutch 110 is modeled after the triceps surae muscle group (calf muscles). Apparatus 100 allows for a controlled energy storage and return, while reducing the forces the actual human body must generate. As set forth above, there are five main stages of walking that apparatus 100 responds to: heel strike, foot flat, stance dorsiflexion, stance plantar flexion (propulsion), and swing phase. Due to the linkage between the clutch 110 and the frame 102, the exoskeleton is able to adjust to these events. Right before heel strike, clutch 110 engages. As the foot plantar flexes to the foot flat position, clutch 110 uses its internal springs to take up the remaining slack in the system, ensuring the elastic element 112 is taught, but not yet stretched beyond its resting length. As the foot reaches the foot flat position, clutch 110 locks, causing a rigid attachment for elastic element 112 to stretch against. As dorsiflexion begins, the user's center of mass energy is transmitted to elastic element 112, which deforms to store strain energy. As push-off occurs, the stored energy is then returned to the user to assist ankle propulsion. At the end of push-off, a timing mechanism causes clutch 110 to disengage and allows for free ankle rotation during the swing phase of walking, thus allowing the user to reposition for the next heel strike.

Embodiments of the AFO device described herein may constructed by manufacturing a light weight frame, a clutch, and an elastic element. Frame 102 can be made from a variety of rigid or semi-rigid composite, plastic, or light weight metal materials. The prototypes produced so far are primarily composed of carbon fiber, fiberglass, Kevlar, and aluminum composites. The frame's ergonomically designed components come from composite laminations designed to comfortably transmit forces to and from the user. The elastic component can be made from many materials: spring steel, elastic polymers, rubber, S-glass, E-glass, carbon fiber, Kevlar, or a composite of those or other elastic materials. Clutch 110 may be made from lightweight aluminum, steel, brass, plastic, and metal compounds. These materials make up the gears, mechanical constraints, bearings, and structure of clutch 110. Linkage 114 between clutch 110 and elastic element 112 can be made from a variety of cord, wire, or other linkages such as, Kevlar, or metal attachments. All together these components can be assembled into a working passive-elastic ankle exoskeleton.

A user simply puts on the exoskeleton to assist during normal walking. Because device function is coupled to natural movement once it is set for a user, the user is only required to initiate locomotion to benefit from assistance. The device works by passively storing energy from an individual's center of mass, specifically during the initial stance phase of walking, running, or locomotion, and returns the stored energy to assist during the push-off phase of walking, running, or locomotion. This does not require additional effort from the user. It takes advantage of passive components (spring or elastic elements) to store and return energy at set periods. The energy storage and return is controlled by a mechanical clutch that adjusts to the user's gait and controls the periods of energy storage and return. By linking these components it is possible to bring lightweight, portable assistance to locomotion without any external sources of power (batteries, motors, or power sources). Apparatus 100 can be used as a recreational aid to assist locomotion of individuals with normal ankle joint function. Apparatus 100 can also be used to assist locomotion of individuals with impaired lower leg function, for example, due to stroke, cerebral palsy, musculoskeletal injury, or other impairment or disorder.

In some of the embodiments described herein, the device is a completely passive, completely mechanical, clutched ankle exoskeleton, designed to assist locomotion by aiding forward propulsion and reduce the metabolic cost of walking by decreasing oxygen consumption.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. An apparatus for using controlled storage and release of mechanical energy to aid in locomotion, the apparatus comprising:
   a frame including an upper portion configured to mechanically couple to a leg of a subject on a calf side of an ankle joint of the subject and a lower portion pivotally attached to the upper portion configured to mechanically couple to a foot of the subject on a foot side of the ankle joint of the subject; and
   a rotary clutch and an elastic element coupled between the upper and lower portions of the frame to control periods of energy storage and release by the elastic element, wherein the rotary clutch includes a rotatable drum, a ratchet coupled to the rotatable drum, a pawl, and first and second structures located on the rotatable drum to selectively engage and disengage the pawl from the ratchet.

2. The apparatus of claim 1, wherein the upper portion of the frame is configured to fit around at least a portion of the calf of the subject and wherein the lower portion is configured to surround at least a portion of the foot of the subject.

3. The apparatus of claim 2, wherein the upper and lower portions are coupled to each other via hinges that allow dorsiflexion and plantar flexion of the ankle joint of the subject.

4. The apparatus of claim 2, wherein the lower portion of the frame comprises a shoe.

5. The apparatus of claim 2, wherein the lower portion of the frame is configured to attach to a shoe.

6. The apparatus of claim 1, wherein the clutch is coupled to the upper portion of the frame and the elastic element is coupled to the lower portion and to the clutch.

7. The apparatus of claim 1, wherein the elastic element is coupled to the clutch via a linkage that is less resilient than the elastic element in a direction of intended application of force to the elastic element.

8. The apparatus of claim 7, wherein the linkage comprises a cord that is coupled to the drum such that rotation of the drum extends and retracts the cord.

9. The apparatus of claim 1, wherein the elastic element comprises a coil spring or an elongate elastomeric member that stretches in a direction of applied force.

10. The apparatus of claim 1, wherein the elastic element comprises a resilient material that bends in a direction of applied force.

11. The apparatus of claim 1, wherein the clutch is configured to engage before heel strike of the individual's foot, to lock during a foot flat position of the individual's foot such that the elastic element stores mechanical energy during dorsiflexion of the ankle joint and releases the stored energy during push off of the individual's foot, and wherein the clutch is configured to release during or after the push off to allow free rotation of the ankle joint during foot swing of the individual's foot.

12. The apparatus of claim 1, wherein the pawl includes a structure having a first side facing a first direction and a second side facing a second direction different from the first direction and the clutch includes a detent mechanism for engaging the pawl on the first side or the second side for holding the pawl in engagement with or away from the ratchet.

13. The apparatus of claim 1, wherein the clutch is configured to engage, lock, and disengage in response to a biological signal from the subject.

14. The apparatus of claim 13, wherein the biological signal comprises an electromyography signal.

15. The apparatus of claim 1, wherein the periods of energy storage and release controlled by the clutch are adjustable according to a gait of the individual.

16. The apparatus of claim 1, wherein the first and second structures include a first timing pin for engaging the ratchet with the pawl and a second timing pin for releasing the ratchet from the pawl.

17. The apparatus of claim 16, wherein positions of the timing pins are adjustable to change the periods of energy storage and release.

18. The apparatus of claim 1, wherein the frame comprises an exoskeleton.

19. The apparatus of claim 1, wherein the frame, clutch, and elastic member form an ankle foot orthotic (AFO) device.

* * * * *